United States Patent
Won

(10) Patent No.: US 9,128,050 B2
(45) Date of Patent: Sep. 8, 2015

(54) APPARATUS AND METHOD FOR INSPECTING GRAPHENE BOARD

(71) Applicant: SAMSUNG TECHWIN CO., LTD., Changwon (KR)

(72) Inventor: Dong-kwan Won, Changwon (KR)

(73) Assignee: Hanwha Techwin Co., Ltd., Changwon-si (KR)

( * ) Notice: Subject to any disclaimer, the term of this patent is extended or adjusted under 35 U.S.C. 154(b) by 189 days.

(21) Appl. No.: 13/690,051

(22) Filed: Nov. 30, 2012

(65) Prior Publication Data

US 2013/0265567 A1    Oct. 10, 2013

(30) Foreign Application Priority Data

Apr. 9, 2012   (KR) .................. 10-2012-0036800
Aug. 8, 2012   (KR) .................. 10-2012-0086942

(51) Int. Cl.
| | |
|---|---|
| G01N 21/59 | (2006.01) |
| G01B 11/04 | (2006.01) |
| G01N 21/956 | (2006.01) |
| G01B 11/14 | (2006.01) |
| G01B 11/02 | (2006.01) |
| G01N 21/95 | (2006.01) |

(52) U.S. Cl.
CPC .............. *G01N 21/59* (2013.01); *G01B 11/02* (2013.01); *G01B 11/046* (2013.01); *G01B 11/14* (2013.01); *G01N 21/9501* (2013.01); *G01N 21/956* (2013.01); *G01N 2021/95676* (2013.01)

(58) Field of Classification Search
None
See application file for complete search history.

(56) References Cited

U.S. PATENT DOCUMENTS

| | | | |
|---|---|---|---|
| 2003/0210402 A1* | 11/2003 | Libinson et al. | 356/484 |
| 2005/0018716 A1* | 1/2005 | Mueller et al. | 372/9 |
| 2009/0225390 A1* | 9/2009 | Lin et al. | 359/239 |
| 2010/0033735 A1* | 2/2010 | Sakai et al. | 356/632 |
| 2010/0142225 A1* | 6/2010 | Kurihara et al. | 362/621 |
| 2013/0122614 A1* | 5/2013 | Chen et al. | 438/16 |

FOREIGN PATENT DOCUMENTS

| | | |
|---|---|---|
| JP | 11-101614 A | 4/1999 |
| JP | 2007-065561 A | 3/2007 |
| JP | 2010-175433 A | 8/2010 |

* cited by examiner

*Primary Examiner* — Gordon J Stock, Jr.
(74) *Attorney, Agent, or Firm* — Sughrue Mion, PLLC

(57) ABSTRACT

An apparatus and method for inspecting a graphene board. The graphene board inspecting apparatus for inspecting a graphene board on which at least one graphene layer is formed includes: a light processing unit which emits at least one light on the graphene board, receives the at least one light penetrating the graphene board and converts the received at least one light to an output signal; a transmittance detecting unit which receives the output signal from the light processing unit to inspect a transmittance of the at least one light penetrating the graphene board; and a determination unit which is connected to the transmittance detecting unit and receives the detected transmittance to determine a state of the graphene board by analyzing the detected transmittance.

17 Claims, 9 Drawing Sheets

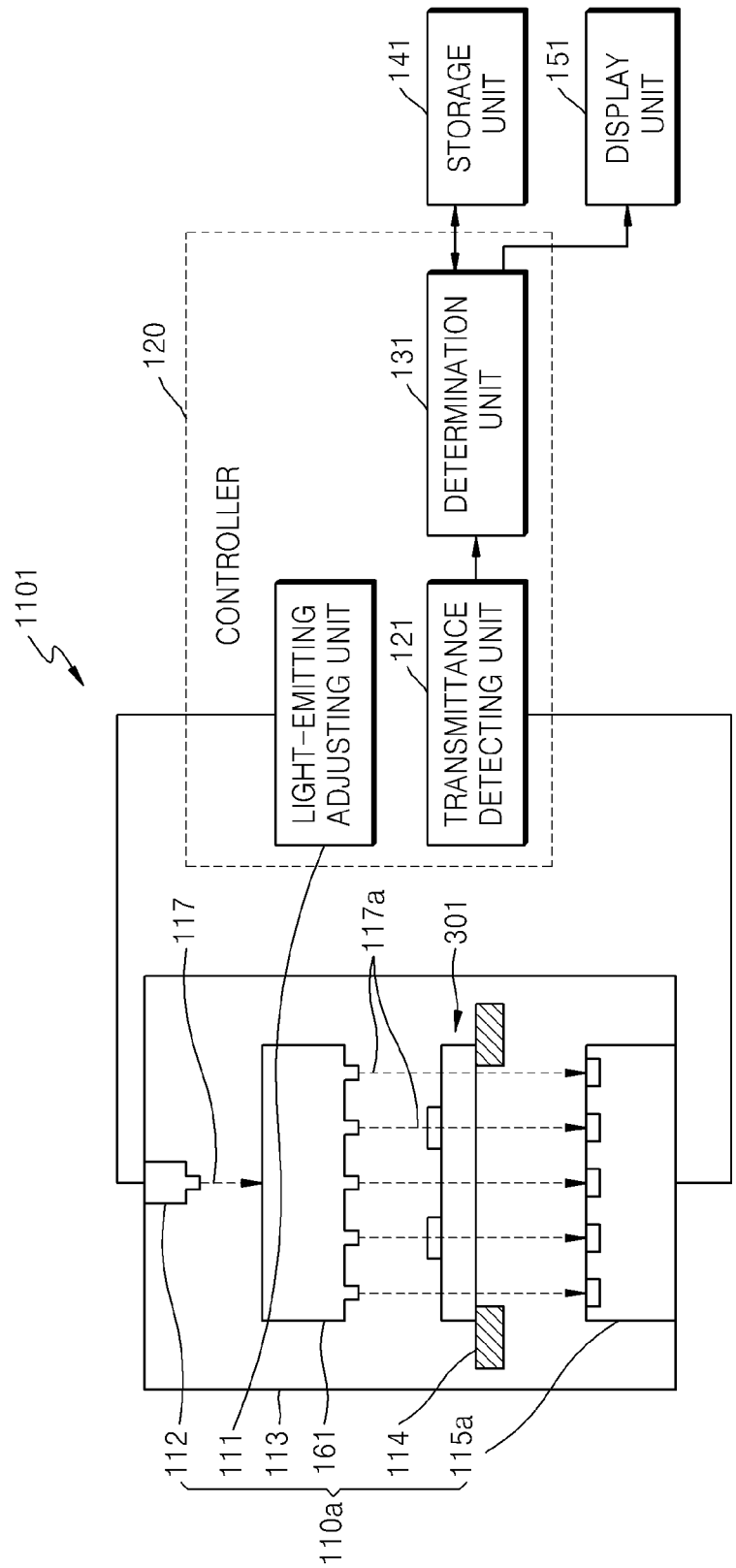

APPARATUS AND METHOD FOR INSPECTING GRAPHENE BOARD

CROSS-REFERENCE TO RELATED PATENT APPLICATIONS

This application claims priority from Korean Patent Application No. 10-2012-0036800, filed on Apr. 9, 2012 and Korean Patent Application No. 10-2012-0086942, filed on Aug. 8, 2012, in the Korean Intellectual Property Office, the disclosures of which are incorporated herein in their entirety by reference.

BACKGROUND

1. Field

Apparatuses and methods consistent with exemplary embodiments relate to measuring of instruments, and more particularly, to inspecting a graphene board in which graphene is formed.

2. Description of the Related Art

With development of semiconductor technology, development on a new material is being actively performed. In particular, research into materials including carbon, for example, a carbon nanotube, a diamond, graphite, graphene, and the like are being conducted. Specifically, graphene, which is a nano material including carbon, has an electrical conductivity equal to or higher than 100 times than copper and may rapidly transfer electrons at a speed equal to or higher than 100 times than silicon. Thus, graphene has been gradually replaced by a conductive material of an electronic apparatus, and a graphene board may be one. The graphene board has a state where a graphene layer formed on a substrate formed of an insulating material is patterned.

A method of inspecting a graphene board has been disclosed in Japanese Laid-Open Patent Publication No. 2010-175433. In detail, the Japanese Laid-Open Patent Publication discloses a method of determining whether a transparent conductive film exists by radiating ultraviolet (UV) rays on the transparent conductive film. However, a more detailed method is required to inspect a graphene board.

SUMMARY

One or more exemplary embodiments provide an apparatus and method for inspecting a state of a graphene board.

According to an aspect of an exemplary embodiment, there is provided a graphene board inspecting apparatus for inspecting a graphene board on which at least one graphene layer is formed, the graphene board inspecting apparatus including: a light processing unit which emits at least one light on the graphene board, receives the at least one light penetrating the graphene board and converts the received at least one light to an output signal; a transmittance detecting unit which receives the output signal from the light processing unit to inspect a transmittance of the at least one light penetrating the graphene board; and a determination unit which is connected to the transmittance detecting unit and receives the detected transmittance to determine a state of the graphene board by analyzing the detected transmittance.

Each of the at least one light may have wavelengths of 380 to 780 nm.

The graphene board may be inspected at a location where external light is blocked.

The light processing unit may include: a chamber having an inner space sealed to block an external light; a substrate supporting member disposed in the chamber and having the graphene board installed thereon; a light-emitting device disposed above the substrate supporting member and emitting the at least one light on the graphene board; and a light-receiving device disposed below the substrate supporting member and receiving the at least one light penetrating the graphene board.

The light-emitting device may be disposed at a top of the chamber. The light-receiving device may be disposed at a bottom of the chamber.

The at least one light emitted from the light-emitting device may penetrate the graphene board in a vertical direction.

The substrate supporting member may move the graphene board in a horizontal direction.

The determination unit may include: a data calculating unit which calculates a width of the at least one graphene layer and a pitch between the at least one graphene layer by analyzing the detected transmittance; and a classifying unit which classifies the graphene board as a good graphene board and a defective graphene board by analyzing the detected transmittance.

A patterning unit for patterning the at least one graphene layer formed in the graphene board may be disposed at a front end of the graphene board inspecting apparatus.

The graphene board may include a transparent material through which the at least one light emitted from the light processing unit penetrates.

The light processing unit may include: a light-emitting device emitting a light; a light-dividing unit which divides the light emitted from the light-emitting device into the at least one light comprising a plurality of lights, and emits the divided at least one light to the graphene board; and a light-receiving device receiving the at least one light penetrating the graphene board.

According to an aspect of another exemplary embodiment, there is provided a method of inspecting a graphene board, the method including: preparing the graphene board on which at least one graphene layer is formed on a substrate; emitting at least one light to the graphene board; detecting a transmittance of the at least one light penetrating the graphene board; and determining a state of the graphene board by analyzing the detected transmittance.

The at least one light may have a wavelength of 380 to 780 nm.

The method may further include measuring a width of the at least one graphene layer formed on the graphene board and a pitch between the at least one graphene layer by analyzing the transmittance of the at least one light.

BRIEF DESCRIPTION OF THE DRAWINGS

The above and other aspects will become more apparent by describing in detail exemplary embodiments with reference to the attached drawings, in which:

FIG. 11 is a block diagram of a graphene board inspecting apparatus in which a graphene board is installed, according to another exemplary embodiment;

DETAILED DESCRIPTION OF THE EXEMPLARY EMBODIMENTS

Figure 1:
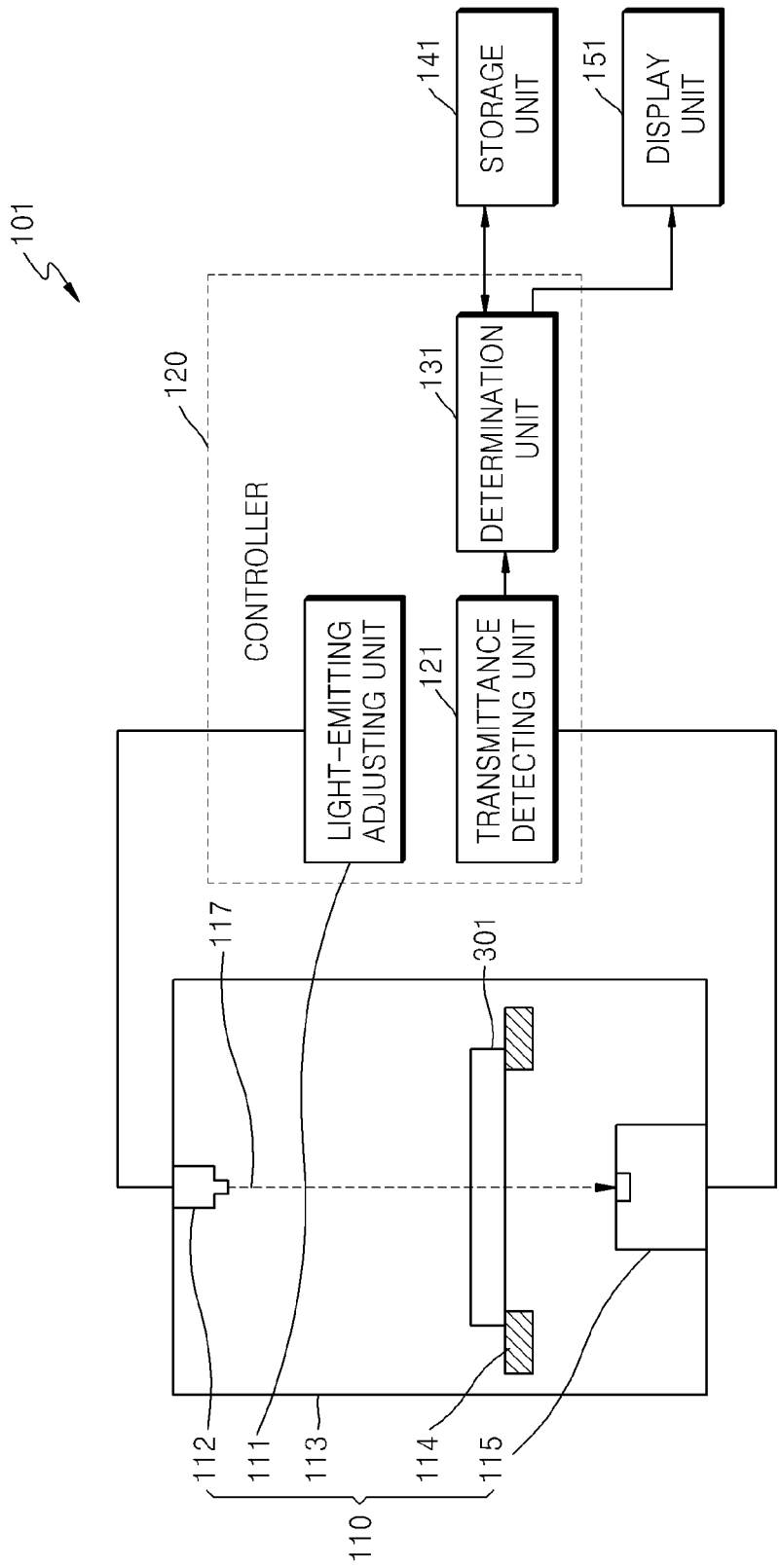
FIG. 1 is a schematic block diagram of a graphene board inspecting apparatus in which a graphene board is installed, according to an exemplary embodiment.

Now, exemplary embodiments according to the inventive concept will be described in detail with reference to the accompanying drawings. The same reference numerals in the drawings may denote the same elements.

FIG. 1 is a schematic block diagram of a graphene board inspecting apparatus 101 in which a graphene board 301 is installed, according to an exemplary embodiment. Referring to FIG. 1, the graphene board inspecting apparatus 101 includes a light processing unit 110, a transmittance detecting unit 121, a determination unit 131, a storage unit 141, and a display unit 151. The graphene board inspecting apparatus 101 inspects a state of the graphene board 301. In other words, the graphene board inspecting apparatus 101 determines whether the graphene board 301 is in a good or bad state by inspecting the graphene board 301 with light.

Figure 3:
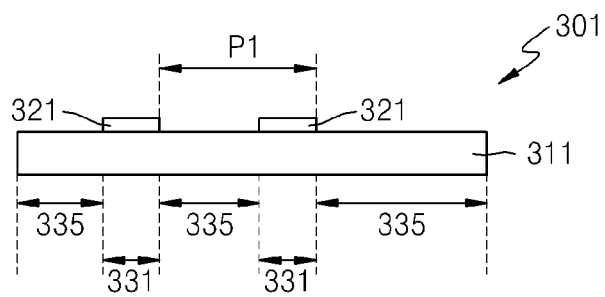
FIG. 3 is a cross-sectional view of a graphene board inspected by the graphene board inspecting apparatus of FIG. 1, according to an exemplary embodiment.

FIG. 3 is a cross-sectional view of the graphene board 301. Referring to FIG. 3, the graphene board 301 includes a substrate 311 and graphene layers having specific patterns and formed on the substrate 311. In other words, the substrate 311 includes a region 331 where a graphene layer 321 is formed and a region 335 where a graphene layer 321 is not formed. Thus, if light is emitted onto the graphene board 301, a transmittance of light penetrating the region 331 where the graphene layer 321 is formed and a transmittance of light penetrating the region 335 where the graphene layer 321 is not formed are different from each other. The graphene board inspecting apparatus 101 inspects the graphene board 301 by using this fact.

The substrate 311 may be formed of a material through which light may penetrate and does not conduct electricity, for example, at least one material selected from the group consisting of polypropylene, polyethylene terephthalate (PET), polyethylene terephthalate glycol (PETG), and polycarbonate.

The light processing unit 110 emits light to the graphene board 301, receives light penetrating the graphene board 301, converts the received light into an electrical signal, and outputs the electrical signal. Light emitted to the graphene board 301 may have rays having wavelengths of 380 to 780 nm. In particular, when the rays have wavelengths of 550 nm, the light penetrating the graphene board 301 has the highest transmittance. Accordingly, visible rays having wavelengths of 550 nm may be preferably used to inspect the graphene board 301. However, the inventive concept is not limited thereto, and rays which can measure transmittance of light penetrating the graphene board 301 including radiation rays, UV light, or a laser may be used.

Figure 4:
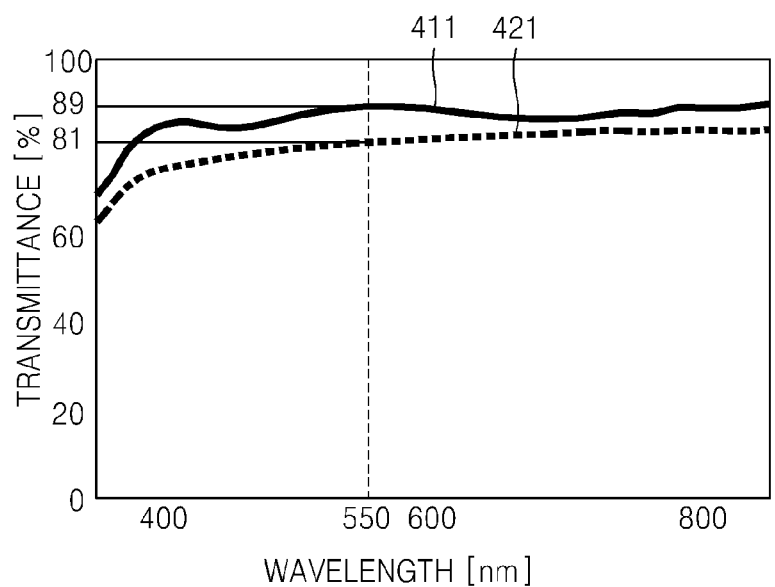
FIG. 4 is a graph showing a transmittance of light penetrating the graphene board, according to an exemplary embodiment.

FIG. 4 is a graph showing a transmittance of light penetrating the graphene board 301. Referring to FIG. 4, a transmittance 421 of light penetrating the region 331 (see FIG. 3) where the graphene layer 321 is formed is different from a transmittance 411 of light penetrating the region 335 (see FIG. 3) where the graphene layer 321 is not formed. In other words, the transmittance 421 of the light penetrating the region 331 where the graphene layer 321 is formed is lower than the transmittance 411 of the light penetrating the region 335 where the graphene layer 321 is not formed. Also, a transmittance of light varies according to wavelengths of light. For example, if a wavelength of light is 550 nm, a transmittance of light penetrating the graphene board 301 is the highest. In detail, when light has a wavelength of 550 nm, the transmittance 421 of the light penetrating the region 331 where the graphene layer 321 is formed is 81%, and the transmittance 411 of the light penetrating the region 335 where the graphene layer 321 is not formed is 89%. As such, a state of the graphene board 301 may be inspected with light having a wavelength of 550 nm.

The light processing unit 110 includes a chamber 113, a substrate supporting member 114, a light-emitting adjusting unit 111, a light-emitting device 112, and a light-receiving device 115.

The chamber 113 has a sealed inner space so that light may not enter the chamber 113 from the outside. The graphene board 301 to be inspected is installed inside the chamber 113. By preventing light from entering the chamber 113 from the outside, a transmittance of the light may be precisely measured when emitting light to the graphene board 301. An inlet (not shown) through which the graphene board 301 enters and an outlet (not shown) through which the graphene board 301 exits are formed in the chamber 113. The chamber 113 may be formed to have any of various shapes, for example, a quadrangular barrel shape or a cylindrical shape.

The substrate supporting member 114 may be disposed in the middle of the inside of the chamber 113. The graphene board 301 is installed on the substrate supporting member 114. The graphene board 301 may be maintained in a horizontal position during inspection. Accordingly, the substrate supporting member 114 is supported horizontally to maintain the graphene board 301 in a horizontal position. The graphene board inspecting apparatus 101 may perform inspection on various regions of the graphene board 301. Accordingly, the substrate supporting member 114 may have a structure in which the graphene board 301 may be easily moved in a horizontal direction.

The substrate supporting member 114 may be configured as a conveyer or a roll-to-roll type member to easily move the graphene board 301. If the substrate supporting member 114 is configured as a roll-to-roll type member, the substrate supporting member 114 includes a roller for transportation (not shown), a supply reel (not shown), and a reception reel (not shown). The roller for transportation transfers the graphene board 301 wound on the supply reel toward the outlet of the chamber 113 from the inlet of the chamber 113.

The substrate supporting member 114 may transfer the graphene board 301 at a constant speed or may temporarily stop the graphene board 301. In other words, when the graphene board inspecting apparatus 101 inspects many graphene boards 301, the substrate supporting member 114 transfers the installed graphene board 301 at a constant speed, but when the graphene board inspecting apparatus 101 inspects the graphene board 301 more accurately, there is a need to stop the graphene board 301 for a predetermined period of time. For this, the substrate supporting member 114 may move the installed graphene board 301 at a constant speed or may temporarily stop the graphene board 301.

The substrate supporting member 114 may be configured to be moved not only in a horizontal direction but also in horizontal and vertical directions so as to inspect various regions of the graphene board 301. At this time, the light-emitting device 112 and the light-receiving device 115 are fixed to one place. According to an exemplary embodiment, the light processing unit 110 may include two or more light-emitting devices 112 and/or two or more light-receiving devices 115.

In addition to the graphene board 301, various other members in which transmittance is to be measured may be installed on the substrate supporting member 114.

The light-emitting adjusting unit 111 controls an operation of the light-emitting device 112. The light-emitting adjusting unit 111 sets a type, intensity, wavelength, etc. of light emitted from the light-emitting device 112. The type, intensity, wavelength, etc. of light may be changed during use of the light-emitting device 112 by a user after being initially set.

The light-emitting device 112 is disposed above the substrate supporting member 114, that is, at a top of the chamber 113. The light-emitting device 112 emits light to the graphene board 301 if the graphene board 301 is installed on the substrate supporting member 114. The light emitted from the light-emitting device 112 needs to penetrate the region 331 where the graphene layer 321 is formed and the region 335 where the graphene layer 321 is not formed, that is, between the graphene layers 321 (see FIG. 3). Accordingly, a width of the light emitted from the light-emitting device 112 is formed less than a pitch P1 between the graphene layers 321 or widths of the graphene layers 321.

Figure 5:
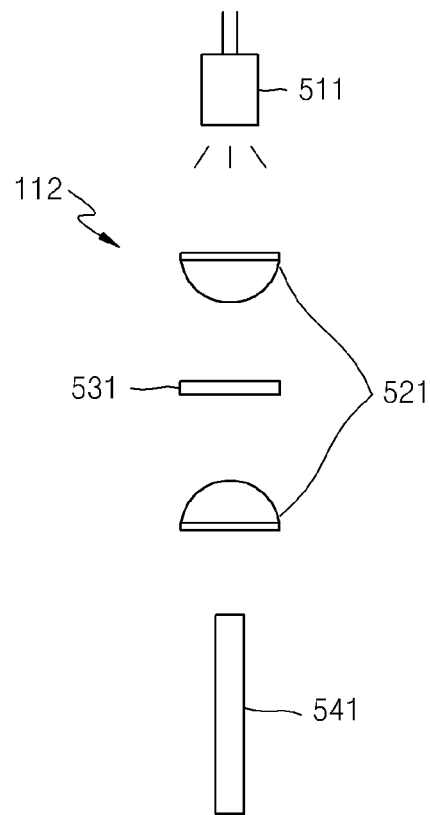
FIG. 5 shows a structure of a light-emitting device shown in FIG. 1, according to an exemplary embodiment.

Referring to FIG. 5, the light-emitting device 112 may include a light source 511, a condenser lens 521, a selecting filter 531, and a planarizing lens 541. The light source 511, the condenser lens 521, the selecting filter 531, and the planarizing lens 541 are arranged in a vertical direction. The light source 511 generates light and emits the generated light to the condenser lens 521. The condenser lens 521 makes incident light into parallel light and outputs the parallel light. The selecting filter 531 transmits only a specific wavelength light from among different wavelength lights penetrating the condenser lens 521, for example, a visible ray having a wavelength of 550 nm. The planarizing lens 541 receives light penetrating the condenser lens 521, planarizes the light, and transmits the light to the substrate supporting member 114. In other words, an intensity of light penetrating the planarizing lens 541 becomes constant. The planarizing lens 541 may be formed of a rod lens of a flyeye lens.

The light-emitting device 112 may irradiate a laser. At this time, the light-emitting device 112 may sequentially include a scanning optical system (not shown), a propagation optical system (not shown), and an object lens (not shown) between the light source 511 and the substrate supporting member 114. The scanning optical system makes a laser irradiated from the light source 511 into a laser beam and irradiates the laser beam by including one of an acoustic optical device, a galvano minor, and a polygon mirror. The propagation optical system propagates the laser beam by including a synthetic quart lens. The object lens converts the laser beam irradiated from the propagation optical system into a smaller laser beam.

Figure 6:
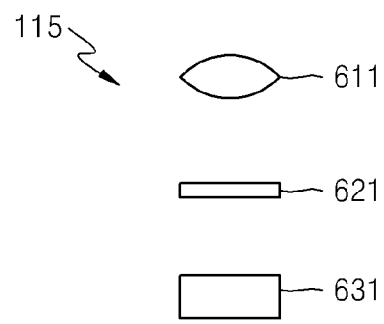
FIG. 6 shows a structure of the light-receiving device shown in FIG. 1, according to an exemplary embodiment.

The light-receiving device 115 is disposed below the substrate supporting member 114, that is, at a bottom of the chamber 113. The light-receiving device 115 and the light-emitting device 112 are disposed on the same vertical line so that the light-receiving device 115 may receive light emitted from the light-emitting device 112 and penetrating the graphene board 301. The light-receiving device 115 converts the received light into an electrical signal and outputs the electrical signal. Referring to FIG. 6, the light-receiving device 115 may include a collector lens 611, a filter 621, and a photoelectric conversion device 631. The collector lens 611, the filter 621, and the photoelectric conversion device 631 are arranged below the substrate supporting member 114 in a vertical direction. The collector lens 611 collects light penetrating the graphene board 301 and transmits the collected light to the filter 621. The filter 621 transmits only light having a wavelength that is the same as that of light emitted from the light-emitting device 112 and blocks other lights having wavelengths different from that of the light emitted from the light-emitting device 112. The photoelectric conversion device 631 converts light penetrating the filter 621 into an electrical signal and outputs the electrical signal. The photoelectric conversion device 631 may include a photodiode. The photoelectric conversion device 631 may have an ability to detect minute light and a rapid response speed.

The light-emitting device 112 and the light-receiving device 115 may be formed to move in a horizontal direction to inspect various regions of the graphene board 301. At this time, the substrate supporting member 114 is fixed to one location.

The transmittance detecting unit 121 receives a signal output from the light-receiving device 115 and detects transmittance of light penetrating the graphene board 301.

Figure 2:
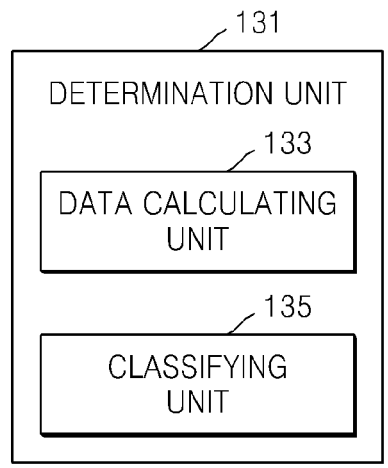
FIG. 2 is a block diagram of a determination unit shown in FIG. 1, according to an exemplary embodiment.

The determination unit 131 receives a transmittance detecting signal output from the transmittance detecting unit 121 and determines a state of the graphene board 301. In other words, the determination unit 131 determines whether states of the graphene layers 321 (see FIG. 3) and states of substrates between the graphene layers 321 are good or bad. Referring to FIG. 2, the determination unit 131 includes a data calculating unit 133 and a classifying unit 135.

The data calculating unit 133 receives light detected by the transmittance detecting unit 121 and calculates widths of the graphene layers 321 (see FIG. 3) and the pitch P1 (see FIG. 3) between the graphene layers 321. The pitch used in the present embodiment refers to the pitch P1 of FIG. 3, and also refers to the sum of one line width of the region 335 where a graphene layer 321 is not formed and one line width of the graphene layers 321. When inspecting the graphene board 301 while moving the graphene board 301, light is emitted to an end and the other end of the graphene layer 321 to measure a moving distance of the graphene board 301, and the width of the graphene layer 321 may be calculated by using the measured moving distance of the graphene board 301. The pitch P1 between the graphene layers 321 may be measured by using the same method.

Also, the classifying unit 135 receives a transmittance of light detected by the transmittance detecting unit 121 and determines a state of the graphene board 301. In other words, if the state of the graphene board 301 is good, a transmittance of the light penetrating the region 331 where the graphene layer 321 is formed is 81%, and transmittance of the light penetrating the region 335 where the graphene layer 321 is not formed is 89%. However, if the graphene board 301 includes an abnormal part, the transmittance of the light penetrating the region 331 where the graphene layer 321 is formed may be higher than 81%, the transmittance of the light penetrating the region 335 where the graphene layer 321 is not formed may be lower than 89%.

Figure 7A:
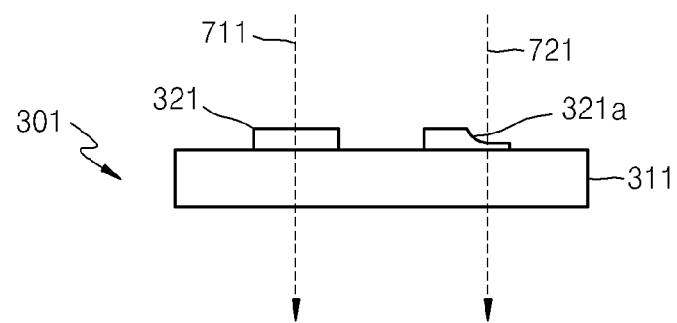
FIG. 7A is a cross-sectional view of a graphene board in which a part of a graphene layer formed relatively lower, according to an exemplary embodiment.
Figure 7B:
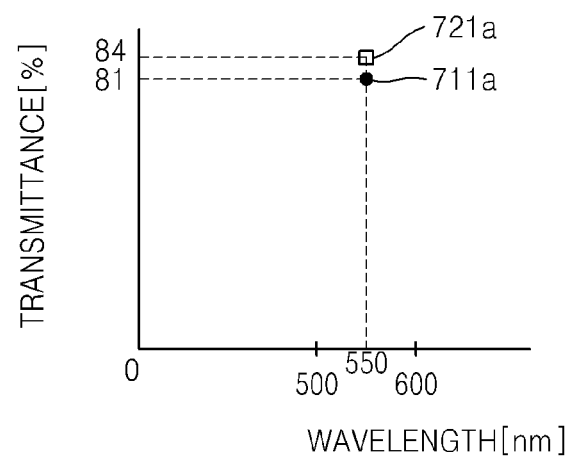
FIG. 7B is a graph showing a transmittance of light penetrating the graphene board of FIG. 7A, according to an exemplary embodiment.

Referring to FIGS. 7A and 7B, when the graphene board 301 includes a graphene layer 321a formed lower than a regulation, a transmittance 721a of a light 721 penetrating the graphene layer 321a may be higher than a transmittance 711a of a light 711 penetrating the graphene layer 321 that is in a normal state, for example, a transmittance of about 84%.

Figure 8A:
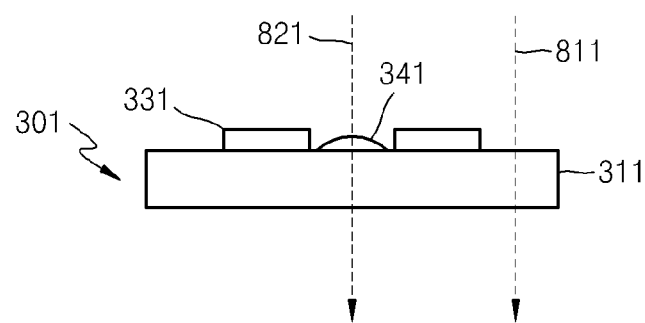
FIG. 8A is a cross-sectional view of a graphene board including waste products of graphene in an area where a graphene layer is not formed, according to an exemplary embodiment.
Figure 8B:
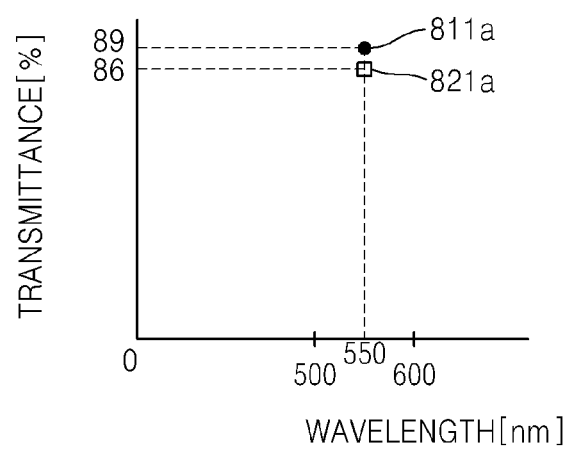
FIG. 8B is a graph showing a transmittance of light penetrating the graphene board of FIG. 8A, according to an exemplary embodiment.

Referring to FIGS. 8A and 8B, if a region where the graphene layer 321 is not formed includes a waste product 341 of graphene, a transmittance 821a of a light 821 penetrating the waste product 341 may be lower than a transmittance 811a of a light 811 penetrating a region where the graphene layer 321 is not formed, for example, a transmittance of about 86%. If the waste product 341 of graphene is a foreign substance instead of graphene, a transmittance of light may be lower than 84%.

Figure 9A:
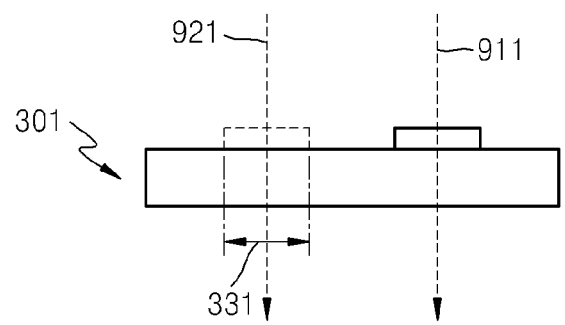
FIG. 9A is a cross-sectional view of a graphene board in which a graphene layer is not formed in an area where a graphene layer is to be formed, according to an exemplary embodiment.
Figure 9B:
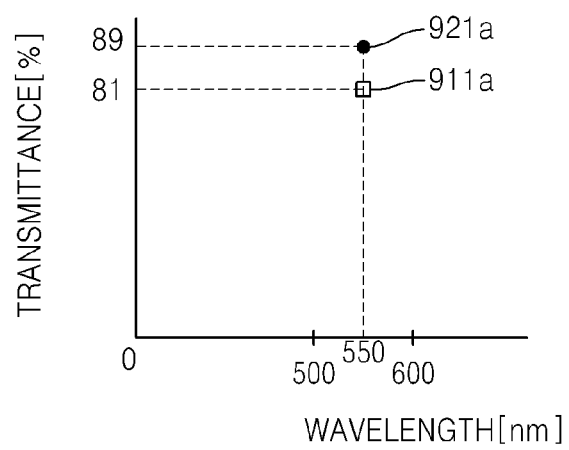
FIG. 9B is a graph showing a transmittance of light penetrating the graphene board of FIG. 9A, according to an exemplary embodiment.

Referring to FIGS. 9A and 9B, when the graphene layer 321 is not formed in the region 331 where a graphene layer is to be formed, a transmittance 921a of a light 921 penetrating the graphene layer 321 is further higher than a transmittance 911a of a light 911 penetrating the graphene layer 321, for example, a transmittance of about 89%.

Figure 10A:
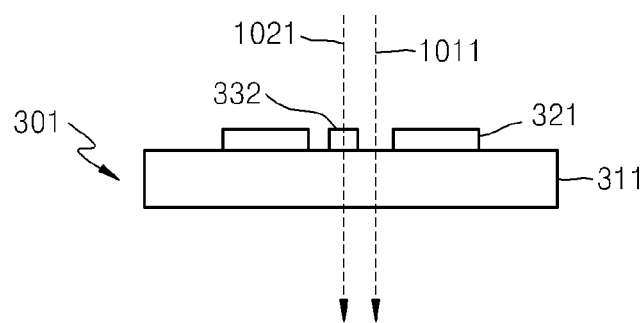
FIG. 10A is a cross-sectional view of a graphene board in which a graphene layer is formed in an area where a graphene layer is not to be formed, according to an exemplary embodiment.
Figure 10B:
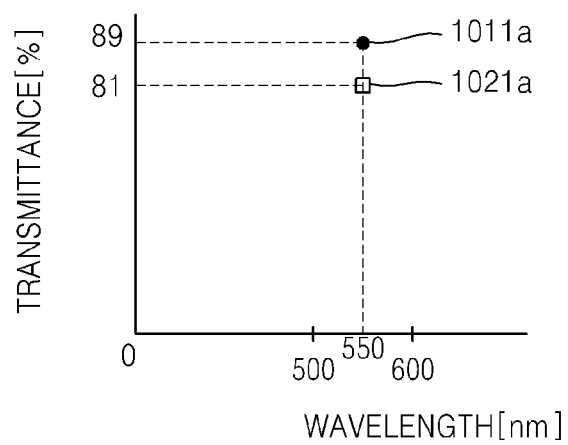
FIG. 10B is a graph showing a transmittance of light penetrating the graphene board of FIG. 10A, according to an exemplary embodiment.

Referring to FIGS. 10A and 10B, when a graphene layer 332 is partially formed in the region 335 where the graphene layer 321 is not to be formed, a transmittance 1021a of a light 1021 penetrating the partial graphene layer 332 may be further lower than a transmittance 1011a of a light 1011 penetrating the region 335 where the graphene layer 321 is not formed, for example, a transmittance of about 81%.

As such, the classifying unit 135 may classify the graphene board 301 as a defective graphene board when a transmittance of light detected by the transmittance detecting unit 121 is 82 to 88%. In this regard, the classifying unit 135 may set a range of a defect to 83 to 87% in consideration of a deviation of the transmittance.

The light-emitting adjusting unit 111, the transmittance detecting unit 121, and the determination unit 131 may be individually included or may be included in one apparatus, that is, a controller 120.

The storage unit 141 may store data processed by the determination unit 131. The storage unit 141 may be included in the determination unit 131 or the controller 120.

The display unit 151 may display the data processed by the determination unit 131 on a screen. The display unit 151 may be configured as a light-emitting diode (LED) display or a liquid crystal display (LCD).

FIG. 11 is a block diagram of a graphene board inspecting apparatus 1101 in which the graphene board 301 is installed, according to another exemplary embodiment. Referring to FIG. 11, the graphene board inspecting apparatus 1101 includes a light processing unit 110a, a transmittance detecting unit 121, a determination unit 131, a storage unit 141, and a display unit 151. The graphene board inspecting apparatus 1101 shown in FIG. 11 has the same configuration as the graphene board inspecting apparatus 101 of FIG. 1 except the light processing unit 110a, and thus, only the light processing unit 110a will be described to avoid a repeated description.

The light processing unit 110a emits a plurality of rays of light to a front surface of the graphene board 301, receives light penetrating the graphene board 301, converts the light into an electrical signal, and outputs the electrical signal. The light emitted to the graphene board 301 may be rays having wavelengths of 380 to 780 nm, for example, 550 nm. However, the present embodiment is not limited thereto, and radiation rays, UV light, or a laser may be used. The wavelength of the light has been described with reference to FIG. 4, and thus, a repeated description is omitted here.

The light processing unit 110a includes a chamber 113, a substrate supporting member 114, a light-emitting adjusting unit 111, a light-emitting device 112, a light-dividing unit 161, and a light-receiving device 115a. The chamber 113, the substrate supporting member 114, the light-emitting adjusting unit 111, and the light-emitting device 112 have been described with reference to FIG. 1 in detail, and thus, a repeated description is omitted here.

The light-dividing unit may be implemented by a beam splitter which divides light emitted from the light-emitting device 112 into a plurality of rays and emits the plurality of rays of light to the graphene board 301. In other words, the beam splitter emits light to the front surface of the graphene board 301. A width of each of the at least one light is less than a pitch between the at least one graphene layer and a width of each of the at least one graphene layer. As such, by emitting the plurality of rays of light to the front surface of the graphene board 301 by including the beam splitter, the graphene board 301 may be inspected at a time. Accordingly, a time to inspect the graphene board 301 is reduced. In particular, a time to inspect the graphene board 301 having a large-area graphene is significantly reduced.

The light-receiving device 115a is disposed below the substrate supporting member 114, that is, at a bottom of the chamber 113. The light-receiving device 115a and the light-emitting device 112 are disposed on the same vertical line so that the light-receiving device 115a may receive light emitted from the light-emitting device 112 and penetrating the graphene board 301. The light-receiving device 115a receives a plurality of rays of light penetrating the graphene board 301 at the same time. The light-receiving device 115a converts the received light into an electrical signal and outputs the electrical signal.

Referring to FIG. 6, the light-receiving device 115a may include the collector lens 611, the filter 621, and the photoelectric conversion device 631. In this regard, the number of collector lenses 611, filters 621, and photoelectric conversion devices 631 may correspond to the number of rays of light penetrating the graphene board 301. For example, if twenty rays of light penetrate the graphene board 301, twenty collector lenses 611, twenty filters 621, and twenty photoelectric conversion devices 631 may be included.

The collector lens 611 collects light penetrating the graphene board 301 and transmits the collected light to the filter 621. The filter 621 transmits only light having a wavelength that is the same as that of the light emitted from the light-emitting device 112 and blocks other lights having wavelengths different from that of the light emitted from the light-emitting device 112. The photoelectric conversion device 631 converts the light penetrating the filter 621 into an electrical signal and outputs the electrical signal. The photoelectric conversion device 631 may include a photodiode. The photoelectric conversion device 631 may have an ability to detect minute light and a rapid response speed.

The light-dividing unit 161, i.e., the beam splitter, and the light-receiving device 115a may be formed to move in a horizontal direction to inspect various regions of the graphene board 301. At this time, the substrate supporting member 114 is fixed to one location.

Figure 12:
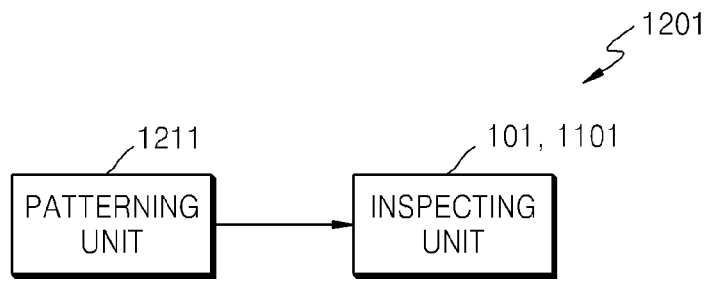
FIG. 12 is a block diagram of a graphene board inspecting apparatus, according to another exemplary embodiment.

FIG. 12 is a block diagram of a graphene board inspecting apparatus 1201, according to another exemplary embodiment. Referring to FIG. 12, the graphene board inspecting apparatus 1201 includes a patterning unit 1211, a plurality of inspecting units 101 and 1101.

The patterning unit 1211 patterns the graphene layer 321 (see FIG. 3) formed on the substrate 311 (see FIG. 3).

A chemical vapor deposition (CVD) method may be used to form the graphene layer 321 on the substrate 311. In other words, a base member in which a metal catalyst layer, such as copper, is formed is put into a chamber (not shown), and gas, including carbon and heat, is applied to the chamber, and thus, the metal catalyst layer absorbs carbon. Then, carbon is separated from the metal catalyst layer by rapidly cooling the base member, and then the carbon is crystallized. Then, the crystallized carbon is transferred to a substrate, and the metal catalyst layer is removed to thus complete the manufacture of the graphene board 301.

The patterning unit 1211 coats a photoresist on the graphene layer 321 (see FIG. 3), masking, exposing, and developing processes are performed on the photoresist, the graphene board 301 is etched, and the photoresist remaining in the graphene board 301 is removed, thereby completing patterning of the graphene layer 321. However, the inventive concept is not limited thereto, and the patterning unit 1211 may pattern the graphene layer 321 by dry etching using plasma or polishing.

The inspecting units 101 and 1101 have the same configurations as the graphene board inspecting apparatuses 101 and 1101 shown in FIGS. 1 and 11, respectively, and thus, a repeated description is omitted here.

As such, as the patterning unit 1211 may be located at a front end of the inspecting units 101 and 1101 so as to immediately inspect the patterned graphene board 301. Accordingly, when the inspecting units 101 and 1101 detect an error in patterning the graphene board 301, the error may be immediately corrected. Thus, a manufacturing time and manufacturing costs of the graphene board 301 may be significantly reduced.

Figure 13:
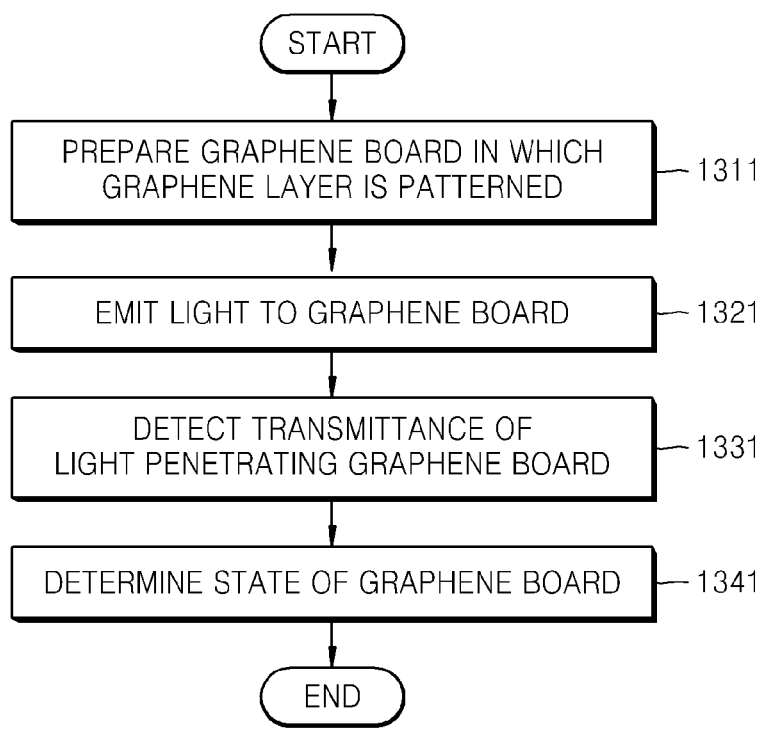
FIG. 13 is a flowchart showing a method of inspecting a graphene board, according to an exemplary embodiment.

FIG. 13 is a flowchart showing a method of inspecting a graphene board, according to an exemplary embodiment. Referring to FIG. 13, the method may include operations 1311 to 1341. The method of inspecting a graphene board will be described with reference to FIGS. 1 to 3.

In operation 1311, the graphene board 301 (see FIG. 3) in which the graphene layer 321 is patterned on the substrate 311 is prepared. In order to prepare the graphene board 301, a process of forming the graphene layer 321 on the substrate 311 and patterning the graphene layer 321 is necessary.

In operation 1321, light 117 is emitted to the graphene board 301. The light 117 (see FIG. 1) emitted to the graphene board 301 may be emitted in a vertical direction or a horizontal direction. The light 117 has a specific wavelength, and light having different wavelengths may be blocked. For this, the graphene board 301 to be inspected may be disposed in a sealed space in which external light is blocked. However, when light has a high straight advancing property, the graphene board 301 may be inspected in an open space.

In operation 1331, a transmittance of the light 117 (see FIG. 1) penetrating the graphene board 301 is inspected. From among the light 117 penetrating the graphene board 301, a transmittance of light penetrating the region 331 (see FIG. 3) where the graphene layer 321 is formed is different from a transmittance of light penetrating the region 335 where the graphene layer 321 is not formed, and thus, there is a need to inspect a precise transmittance.

In operation 1341, a state of the graphene board 301 is determined by analyzing the detected transmittance of light. In other words, widths of the graphene layers 321 (see FIG. 3) and the pitch P1 (see FIG. 3) between the graphene layers 321 are calculated, and shapes of the graphene layers 321 and a shape of the substrate 311 are determined. It is determined whether the graphene board 301 has a defect by using the determined data. In detail, it may be determined whether the graphene board 301 has a defect by calculating the widths of the graphene layers 321 and the pitch P1 between the graphene layers 321 or by determining the shapes of the graphene layers 321 and the shape of the substrate 311.

As described above, a state of the graphene board 301 may be inspected by using visible rays and wavelengths which can measure a transmittance of light penetrating the graphene board 301 on the graphene board 301 and detecting a transmittance of the light 117 penetrating the graphene board 301. In particular, the widths of the graphene layers 321 and the pitch P1 between the graphene layers 321 may be measured by allowing light to penetrate the graphene board 301.

As such, a time to inspect the graphene board 301 may be significantly reduced by inspecting the graphene board 301 by using visible rays and wavelengths which can measure a transmittance of light penetrating the graphene board 301. In particular, a time to inspect the graphene board 301 in which a large-area graphene layer 321 is formed may be greatly reduced.

A state of a graphene board may be inspected by irradiating visible rays on the graphene board and detecting a transmittance of light penetrating the graphene board.

In particular, widths of graphene layers and a pitch between the graphene layers may be measured by detecting a transmittance of light penetrating the graphene board.

As such, a time to inspect the graphene board may be significantly reduced by inspecting the graphene board by using visible rays and wavelengths which can measure a transmittance of light penetrating the graphene board 301. In particular, a time to inspect the graphene board in which a large-area graphene layer is formed may be greatly reduced.

While the inventive concept has been particularly shown and described with reference to exemplary embodiments thereof, it will be understood by those of ordinary skill in the art that various changes in form and details may be made therein without departing from the spirit and scope of the inventive concept as defined by the following claims.

What is claimed is:

1. A graphene board inspecting apparatus for inspecting a graphene board on which a plurality of graphene layers are formed, the graphene board inspecting apparatus comprising:
a light processing unit comprising a light-emitting device, a light-receiving device and a light-dividing unit, wherein the light-emitting device emits a light; the light-dividing unit divides the light emitted from the light-emitting device into a plurality of lights having an identical wavelength and emits the plurality of lights to the graphene board; and the light-receiving device receives the plurality of lights penetrating the graphene board and converts the plurality of lights to a plurality of output signals;
a transmittance detector which receives the plurality of output signals from the light processing unit to inspect a transmittance of the plurality of lights penetrating the graphene board; and
a determiner which is connected to the transmittance detector and receives the detected transmittance to determine a state of the graphene board by analyzing the detected transmittance,
wherein the determiner comprises:
a data calculator which calculates a width of the plurality of graphene layers and a pitch between the plurality of graphene layers using a moving distance of the graphene board in which the width and the pitch are measured by emitting the plurality of lights to the plurality of graphene layers while moving the graphene board and analyzing the detected transmittance; and
a classifier which classifies the graphene board as a good graphene board or a defective graphene board by analyzing the detected transmittance.

2. The graphene board inspecting apparatus of claim 1, wherein the plurality of lights have wavelengths of 380 to 780 nm.

3. The graphene board inspecting apparatus of claim 1, wherein the light processing unit is sealed from outside so that external light is not received at the light processing unit.

4. The graphene board inspecting apparatus of claim 1, wherein a patterner which patterns the plurality of graphene layers formed in the graphene board is disposed at a front end of the graphene board inspecting apparatus.

5. The graphene board inspecting apparatus of claim 1, wherein the graphene board comprises a transparent material through which the plurality of lights emitted by the light processing unit penetrate.

6. The graphene board inspecting apparatus of claim 1, wherein the light-receiving device comprises a plurality of filters which transmit the plurality of lights emitted from the light-dividing unit having a given wavelength, and blocks light having a different wavelength.

7. The graphene board inspecting apparatus of claim 1, wherein a width of each of the plurality of lights is less than the pitch between the plurality of graphene layers and the width of each of the plurality of graphene layers.

8. The graphene board inspecting apparatus of claim 1, wherein the light-emitting device comprises a light source of the light and a selecting filter which transmits light having a given wavelength and blocks light having a different wavelength.

9. The graphene board inspecting apparatus of claim 1, wherein the light processing unit comprises:
a chamber having an inner space sealed to block an external light; and
a substrate supporting member disposed in the chamber and having the graphene board installed thereon,
wherein the light-emitting device is disposed above the substrate supporting member; and
wherein the light-receiving device is disposed below the substrate supporting member.

10. The graphene board inspecting apparatus of claim 8, wherein the light-emitting device further comprises at least one of:
at least one condenser lens which makes the light from the light source to be vertical with respect to the light-receiving unit; and
at least one planarizing lens which planarizes the light.

11. The graphene board inspecting apparatus of claim 9, wherein the light-emitting device is disposed at a top of the chamber.

12. The graphene board inspecting apparatus of claim 9, wherein the light-receiving device is disposed at a bottom of the chamber.

13. The graphene board inspecting apparatus of claim 9, wherein the plurality of lights emitted from the light-emitting device penetrate the graphene board in a vertical direction.

14. The graphene board inspecting apparatus of claim 9, wherein the substrate supporting member moves the graphene board in a horizontal direction.

15. A method of inspecting a graphene board, the method comprising:
preparing the graphene board on which a plurality of graphene layers are formed on a substrate;
emitting a plurality of lights having an identical wavelength to the graphene board;
detecting a transmittance of the plurality of lights penetrating the graphene board;
measuring a width of the plurality of graphene layers and a pitch between the plurality of graphene layers using a moving distance of the graphene board which are measured by emitting the plurality of lights to the plurality of graphene layers while moving the graphene board and analyzing the detected transmittance; and
determining a state of the graphene board by analyzing the detected transmittance.

16. The method of claim 15, wherein the plurality of lights have a wavelength of 380 to 780 nm.

17. The method of claim 15, wherein a width of each of the plurality of lights is less than the pitch between the plurality of graphene layers and the width of each of the plurality of graphene layers.

* * * * *